US011016074B2

(12) United States Patent
 Kahn et al.

(10) Patent No.: US 11,016,074 B2
(45) Date of Patent: May 25, 2021

(54) APPARATUS FOR MEASURING WATER HARDNESS USING ION SELECTIVE ELECTRODE

(71) Applicant: Ecowater Systems LLC, Woodbury, MN (US)

(72) Inventors: Malcolm Kahn, Franklin Lakes, NJ (US); Robert Astle, Middlefield, CT (US); Jeffrey Zimmerman, Forest Lake, MN (US); Ravi Meruva, Lexington, MA (US)

(73) Assignee: Ecowater Systems, LLC, Woodbury, MN (US)

( * ) Notice: Subject to any disclaimer, the term of this patent is extended or adjusted under 35 U.S.C. 154(b) by 132 days.

(21) Appl. No.: 16/369,925

(22) Filed: Mar. 29, 2019

(65) Prior Publication Data

US 2019/0302087 A1    Oct. 3, 2019

Related U.S. Application Data

(60) Provisional application No. 62/649,932, filed on Mar. 29, 2018.

(51) Int. Cl.
  *G01N 33/18*   (2006.01)
  *G01N 27/333*  (2006.01)
  *C02F 1/42*    (2006.01)

(52) U.S. Cl.
  CPC .......... *G01N 33/1853* (2013.01); *C02F 1/42* (2013.01); *G01N 27/333* (2013.01);
  (Continued)

(58) Field of Classification Search
  CPC .......... G01N 33/1853; G01N 33/1813; G01N 33/1893; G01N 27/333; G01N 27/3335;
  (Continued)

(56) References Cited

U.S. PATENT DOCUMENTS

| 3,383,310 A | 5/1968 | Ammer |
| 5,472,590 A | 12/1995 | Yamashita |

(Continued)

FOREIGN PATENT DOCUMENTS

| CN | 103217413 | 7/2013 |
| KR | 20130112346 | 10/2013 |
| WO | 2008073002 | 6/2008 |

OTHER PUBLICATIONS

Tad Patko, Understanding Ion Selective Sensors, Advanced Sensor Technologies, Apr. 2009.

*Primary Examiner* — Benjamin R Schmitt
(74) *Attorney, Agent, or Firm* — DeLio Peterson & Curcio; Robert Curcio (57) ABSTRACT

An apparatus for determining total hardness in a fluid stream utilizing an ion exchange column in a monovalent cationic form having an inlet and an outlet, where one or more monovalent ion selective electrodes are positioned either at an inlet, outlet, or at both locations simultaneously. The monovalent cation selective electrodes are in electrical communication with one another, and in fluid communication with one or more valves incorporated within a fluid path in order to introduce feed water/softened water to the monovalent cation selective electrodes. Additionally, one blending valve may be incorporated in the ion exchange column to allow a fraction of the feed (hard) water to mix with a fraction of the softened water. In this manner, the blending valve may be utilized to adjust the hardness of the water at the output.

22 Claims, 8 Drawing Sheets

(52) U.S. Cl.
CPC ..... *G01N 33/1813* (2013.01); *G01N 33/1893* (2013.01); *C02F 2209/055* (2013.01); *C02F 2303/16* (2013.01)

(58) Field of Classification Search
CPC ... C02F 1/42; C02F 2209/055; C02F 2303/16
See application file for complete search history.

(56) References Cited

U.S. PATENT DOCUMENTS

| | | |
|---|---|---|
| 5,788,826 A | 8/1998 | Nyberg |
| 6,814,872 B2 | 11/2004 | Rawson |
| 9,637,397 B2 | 5/2017 | Averbeck |
| 2004/0188252 A1 | 9/2004 | Chan |
| 2006/0186052 A1 | 8/2006 | Seidel |
| 2007/0175766 A1 | 8/2007 | Holmes |
| 2008/0000771 A1 | 1/2008 | Kakiuchi |
| 2016/0194225 A1 | 7/2016 | Lask et al. |

APPARATUS FOR MEASURING WATER HARDNESS USING ION SELECTIVE ELECTRODE

BACKGROUND OF THE INVENTION

1. Field of the Invention

The present invention relates to an ion-selective electrode that is useful for determining the concentration of ions in a fluid. Specifically, the invention relates to a differential sodium ion selective electrode with a built-in salt bridge, and its use in the determination of sodium ions exchanged during the treatment of hard water.

2. Description of Related Art

Water systems using groundwater as a source are generally concerned with water hardness. As water moves through soil and rock it dissolves small amounts of naturally-occurring minerals and carries them into the groundwater supply. Water is known to be a great solvent for calcium and magnesium, thus if the minerals are present in the soil around a water-supply well, the hard water may be delivered to homes. In this manner, water hardness varies as a function of geography. For example, in areas within the United States where the water is relatively hard, industries might have to spend funds and resources to soften the water, as hard water can damage equipment, fabrics, and clothes.

Furthermore, incoming hardness may fluctuate due to changes in blending of different water sources. For example, in the winter a ground water source may be used, and in the summer a surface water source may be used. The hardness of these water sources most likely differ. Additionally, a municipality generally has more than one well. These wells typically have different hardness concentrations. Depending on which well is supplying water, the hardness in the source water delivered to a water softener will fluctuate. This makes for appreciable variations in feed water hardness.

Calcium and magnesium dissolved in water are the two most common minerals that make water "hard." The degree of hardness becomes greater as the calcium and magnesium content increases and is related to the concentration of multivalent cations dissolved in the water.

The hardness of water is generally referred to by three types of measurements: grains per gallon, milligrams per liter (mg/L), or parts per million (ppm). General guidelines for classification of waters are typically: 0 to 60 mg/L (milligrams per liter) of calcium carbonate is classified as soft; 61 to 120 mg/L is classified as moderately hard; 121 to 180 mg/L is classified as hard; and more than 180 mg/L is classified as very hard.

Table I below depicts the general hardness classification categories of water.

TABLE I

| Grains Per Gallon | Milligrams Per Liter (mg/L) or Parts Per Million (ppm) | Classification |
| --- | --- | --- |
| 0-3.5 | 0-60 | Soft to Slightly Hard |
| 3.5-7.0 | 60-120 | Moderately Hard |
| 7.0-10.5 | 120-180 | Hard |
| over 10.5 | over 180 | Very Hard |

Hard water may form deposits that clog plumbing. These deposits, referred to as "scale", are composed mainly of calcium carbonate ($CaCO_3$), magnesium hydroxide ($Mg(OH)_2$), and calcium sulfate ($CaSO_4$). Calcium and magnesium carbonates tend to be deposited as off-white solids on the inside surfaces of pipes and heat exchangers. This precipitation (formation of an insoluble solid) is principally caused by thermal decomposition of bicarbonate ions but also happens in cases where the carbonate ion is at saturation concentration. The resulting build-up of scale restricts the flow of water in pipes. In boilers, the deposits impair the flow of heat into water, reducing the heating efficiency and allowing the metal boiler components to overheat. In pressurized systems, this overheating can lead to failure.

The presence of ions in an electrolyte, in this case, hard water, can also lead to galvanic corrosion, in which one metal will preferentially corrode when in contact with another type of metal, when both are in contact with an electrolyte.

Conductivity is a measure of water's capability to pass electrical flow. This ability is directly related to the concentration of ions in the water. Conductive ions come from dissolved salts and inorganic materials such as alkalis, chlorides, sulfides, and carbonate compounds. The more ions that are present, the higher the conductivity of water. Likewise, the fewer ions that are in the water, the less conductive it is. Distilled or deionized water can act as an insulator due to its very low (negligible) conductivity value. In contrast, sea water has a very high conductivity.

Conductivity can also measure total dissolved solids (TDS). Total dissolved solids combine the sum of all ionized particles that are generally smaller than 2 microns. This includes all of the disassociated electrolytes that make up salinity concentrations, as well as other compounds such as dissolved organic matter. The higher the level of TDS (ppm), the higher the degree of water hardness. (Using the chart above, 1 grain of hardness is approximately 17.1 ppm (mg/L) in TDS.) This means that the measure of conductivity directly correlates to the measure of ions that contribute to water hardness.

Many consumers use water softeners to soften the water used in their homes, the workplace, schools, etc. These water softeners are typically preset to soften water of a predefined degree of hardness.

In North America and many other countries, the water quality changes seasonally as sources are changed or weather conditions change. Thus, while a customer sets up or performs the initial softener commissioning step in order for the softener to optimally perform at the hardness measured during the installation, any subsequent changes in the feed water will result in poor performance—either the customer will periodically get untreated water or they will have poor water and salt efficiencies.

A water softener includes a resin tank that is filled with resin comprising small beads of cross-lined polystyrene sulfonic acid, and is generally referred to as a cation resin. The resin is usually placed into service with $Na^+$ ions on the beads. When hardness ions come into contact with the $Na^+$ ions bound to the resin, they exchange, or the calcium displaces two Na+ ions, and the $Na^+$ ions are released in the water. Typically, two Na+ ions are exchanged for every one Ca or Mg ion. In addition, iron in the water also exchanges with sodium and reduces the capacity of the water softener.

One problem realized with water hardness in general is the time-variant change of hardness in feed water, such as city feed water. This can be attributed to such configurations as having feed water combined from multiple sources with each source having a different hardness level.

Different methods in the art have been used to measure calcium. For example, in U.S. Pat. No. 6,814,872 issued to Rawson on Nov. 9, 2004 titled "CONTROLLER AND METHOD FOR CONTROLLING REGENERATION OF A WATER SOFTENER," a water hardness indicator is taught in the form of a calcium ion selective electrode. However, it does not teach measuring hardness as a function of divalent elements such as magnesium, barium, strontium, sodium, etc., present in hard water (in flow) and which contribute to water hardness.

Sensors are known in the art for measuring conductivity in a fluid. However, many such sensors have limitations when measuring ionic activity in the fluid. Ion-selective electrodes ("ISE") respond preferentially or selectively to a particular ionic species in a liquid. They are often used in potentiometric measurement of the activity of an ion in a liquid sample. Potentiometric measurement determines the difference in electrical potential between two electrodes which, in contact with a liquid, form an electrochemical cell.

An important part of the measurement is the use of a stable reference electrode. Many ISE's incorporate their own reference electrode; these are usually either a single junction refillable type Ag/AgCl type, or a double junction type, which is used for ISE's such as chloride, bromide, and the like. These types of reference electrodes allow the user to select an appropriate electrolyte for the particular application.

It is desirable to employ a sensor capable of potentiometric determination of the ion content or activity of a sample and the concentration of other components (e.g., glucose, urea, triglycerides, enzymes, drugs) of a sample.

It is also desirable to implement a hardness sensor that does not drift over time, as the employment of such sensors remain active in diverse locations for extended periods of time.

It is further desirable to implement a hardness sensor that requires little or no calibration in order to facilitate installation and on-site operation.

SUMMARY OF THE INVENTION

Bearing in mind the problems and deficiencies of the prior art, it is therefore an object of the present invention to provide an apparatus for measuring water hardness via differential sodium using ion selective electrodes.

It is another object of the present invention to provide an apparatus for measuring water hardness using ion selective electrodes that more precisely quantifies total hardness by considering all divalents present in the hard water.

It is a further object of the present invention to provide an apparatus for measuring water hardness that requires little or no calibration upon installation, and does not appreciably drift over time.

Still other objects and advantages of the invention will in part be obvious and will in part be apparent from the specification, in which in a first aspect, the present invention is directed to a cassette for measuring the total hardness in a fluid stream, comprising: a housing; an ion exchange column or vessel in a monovalent cationic form, the ion exchange column or vessel having an inlet and an outlet separately disposed and extending through the housing; and a monovalent cation selective electrode positioned within the housing at the inlet or the outlet, the monovalent cation selective electrode capable of measuring monovalent cation activity, quantity, or concentration in a fluid stream; wherein hard water flows through the housing via the inlet and outlet to be measured by the monovalent cation selective electrode.

The monovalent cation selective electrode may be coupled to a reference electrode, and/or may be configured to measure sodium ions (Na+).

The cassette may include an internal filling solution within which the monovalent cation selective electrode is encased.

The cassette may further include an ion selective membrane shaped in tubular form to create a 360 degree engagement with a fluid sample flowing therethrough.

In a second aspect, the present invention is directed to a cassette for measuring the total hardness in a fluid stream, comprising: a housing; an ion exchange column or vessel in a monovalent cationic form, the ion exchange column or vessel having an inlet and an outlet separately disposed and extending through the housing; and first and second monovalent cation selective electrodes positioned within the housing and extending therefrom, the first and second monovalent cation selective electrodes capable of measuring monovalent cation activity, quantity, or concentration in a fluid stream; the housing configured into a plurality of chambers, the first and second monovalent cation selective electrodes each housed within one of the plurality of chambers, wherein one of the chambers housing the first monovalent cation selective electrode is filled with an internal solution; a selective membrane shaped to create engagement with a fluid sample flowing therethrough; a dialysis membrane in each of the two chambers forming a salt bridge between the first and second monovalent cation selective electrodes; and an Ag/AgCl pin for each of the first and second monovalent cation selective electrodes.

A salt bridge may be formed by the interfacing of the dialysis membranes between two respective flow paths.

The monovalent cation selective electrodes may be configured to measure sodium ions (Na+).

The internal solution is preferably in constant contact with the first electrode, and comprises a sodium standard solution having a known amount of sodium.

The selective membrane is preferably a sodium membrane.

The selective membrane traverses the cassette vertically, entering through at least one of the plurality of chambers, and extending to the edge of the cassette or outside the cassette.

The cassette may include a valve disposed within a fluid path of the membrane, the valve configured to introduce fluid to at least one monovalent cation selective electrode.

The valve is configured to introduce feed water or softened water to the at least one monovalent cation selective electrode.

The ion exchange column further comprises at least one blending valve to allow a fraction of a hard water fluid stream to mix with a fraction of a softened water fluid stream. The at least one blending valve further adjusts hardness of hard water at the outlet.

The first and second monovalent cation selective electrodes comprise hydrogen, sodium, or potassium.

The salt bridge comprises 2 M KCl to minimize liquid junction potential.

The sodium standard solution may comprise 500 ppm sodium formed in 2 M KCl.

In a third aspect, the present invention is directed to an apparatus for determining hardness in water, the apparatus comprising: a first sodium ISE sensor coupled with a first reference electrode, the first sodium ISE sensor configured to receive hard water; a second sodium ISE sensor coupled with a second reference electrode, the second sodium ISE sensor in electrical communication with the first sodium ISE sensor, and configured to receive soft water; the first and second reference electrodes having a salt bridge therebetween; and at least one drain to receive outflow from effluent fluid from the first and second sodium ISE sensors.

In a fourth aspect, the present invention is directed to an apparatus for determining hardness in water, the apparatus comprising: a first sodium ISE sensor coupled with a first reference electrode, the first sodium ISE sensor configured to receive a standardized sodium solution; a second sodium ISE sensor coupled with a second reference electrode, the second sodium ISE sensor in electrical communication with the first sodium ISE sensor, and configured to receive hard water; the first and second reference electrodes having a salt bridge therebetween; a third sodium ISE sensor configured to receive soft water with exchanged sodium; and at least one drain to receive outflow from effluent fluid from the second and third sodium ISE sensors.

In a fifth aspect, the present invention is directed to an apparatus for determining hardness in water, the apparatus comprising: a first sodium ISE sensor configured to receive hard water; a valve disposed at an outflow path of the first sodium ISE sensor; a drain in fluid communication with the valve; the first sodium ISE sensor encased within a housing containing a standard sodium chloride salt bridge; and a second sodium ISE sensor located outside the housing, the second sodium ISE sensor in electrical communication with the first sodium ISE sensor.

In a sixth aspect, the present invention is directed to an apparatus for measuring the total hardness in water of a water softener, comprising: a housing; an ion exchange column or vessel in a monovalent cationic form, the ion exchange column or vessel having an inlet and an outlet separately disposed and extending through the housing; a monovalent cation selective electrode positioned within the housing at the inlet or the outlet, the monovalent cation selective electrode capable of measuring monovalent cation activity, quantity, or concentration in the water; and a valve for receiving the water from the inlet and/or the outlet; wherein hard water flows through the water softener via the inlet and outlet to be measured by the monovalent cation selective electrode, and the electrode provides an electrical signal commensurate with the amount cation concentration measured at the inlet and at the outlet to provide for a differential measurement of these values in order to ascertain the amount of cation being generated by the softener.

The differential measurement relates to a remaining capacity of the softener to capture and/or exchange hardness ions.

The monovalent cation selective electrode is capable of measuring ionic species that will affect capacity of the softener, including iron that permanently exchanges in a cation resin bed in the softener.

The amount of cation concentration measured at the outlet is a measure of an amount of the cation in the water, such that the apparatus includes a bypass control to allow unsoftened water to be blended to reduce the amount of cation in the water, or to regulate the amount of hardness in the output.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE EMBODIMENT(S)

In describing the embodiment(s) of the present invention, reference will be made herein to FIGS. 1-14 of the drawings in which like numerals refer to like features of the invention.

The present invention may be simplified as an apparatus employing the methodology of U.S. Provisional Patent Application No. 62/649,932, titled "METHOD FOR DETERMINING HARDNESS CONCENTRATION USING A MONOVALENT ION SELECTIVE ELECTRODE" and filed Mar. 29, 2018; the disclosure of which is hereby incorporated by reference.

The present invention is based upon the determination of sodium ion ("Na+") concentrations by sodium ion selective electrodes.

The present invention utilizes an ion specific electrode insomuch as it is beneficial to have a monitor that can measure and/or adjust the hardness measurement value in-situ (real time) after the commissioning step, when the water conditions change. Essentially, in-situ monitoring of water hardness is performed by continuously measuring the sodium ion concentration for water at inlet and outlet of a softener using a sodium ion-selective electrode.

There are advantages to employing ion selective electrodes in a conductivity measurement. For example, the initial set up is inexpensive (typically one only needs a pH/mV meter or Ion meter, the electrodes, a stirring stand, and some basic chemicals); the measurements are unaffected by color or turbidity in the sample; the sample pre-treatment is usually simple; the measurements can be done in "real time", and can be easily automated.

The employed use of ISEs in the present invention is based on the principle of cation exchangers where the divalent ions presented in feed water are exchanged with Na+ ions. The out-flow contains an Na+ ion concentration that is the sum of the original Na+ present in feed water and Na+ ion generated (2 $Na^+$ for each $Ca^{2+}$ or $Mg^{2+}$, $Ba^{2+}$, $Sr^{2+}$)

as a result of the ion exchange. Thus, the total hardness may be calculated by the differential sodium (when the sodium-based ion exchange column is newly regenerated), and the total hardness in moles/grains as $CaCO_3$ (TH)= $([Na^+]_{effluent}-[Na^+]_{influent})/7.86$ where the respective sodium concentrations are in moles/L.

Additionally, when the ion exchange capacity tends to get exhausted, less divalents are exchanged as less Na+ ions are available in the ion-exchanger, at which point the concentration of $Na^+$ ion at the out-flow decreases. Complete exhaustion of the ion exchange column occurs when there are no more $Na^+$ ions available to exchange the divalents. Hence, the $Na^+$ concentration drops to the $Na^+$ ion concentration of in flow (feed water). Thus, for a complete ion exchanger life cycle, the difference between $Na^+$ concentrations at the outflow and inflow varies from maximum to near zero.

An ion-selective electrode ("ISE") is a transducer (or sensor) that converts the activity of a specific ion dissolved in a solution into an electrical potential. The three main components of making a measurement at an ISE are an inner reference, or standard, solution and an outer analyte, or sample, solution separated by a thin membrane.

The voltage is theoretically dependent on the logarithm of the ion activity, as described by the Nernst Equation:

$$E=(2.3026)\cdot(RT/zF)\cdot\log(A)$$

where:
R is the universal gas constant (8.314472 $JK^{-1}$ $mol^{-1}$);
F is the Faraday constant, the number of coulombs per mole of electrons, (9.64853399($10^4$) C $mol^{-1}$);
T is temperature (kelvins);
z is the number of electrons transferred in the cell reaction; and
A is the ratio of ions outside the cell to ions inside the cell.

The sensing part of the electrode is usually made from an ion-specific membrane, coupled together with a reference electrode (either separate or as a combination). ISEs are used where measurements of ionic concentration in an aqueous solution are required.

Typically, a membrane containing an ionophore, is introduced between an "unknown" analyte solution and a "known" reference solution. The ionophore is a neutral "carrier" molecule. The ionophore cannot diffuse out of the membrane but can "trap" the analyte ion at the interface between the solution and membrane. Without the ionophore, the analyte would be unable to partition into the organic membrane. As with the ion-exchange process, equilibrium is established at both solution-membrane interfaces. The resulting charge separation at each interface leads to a phase-boundary potential.

The identity of the membrane determines the selectivity of the electrode. In other words, the type of membrane used dictates which analyte can be detected. Consequently, different electrodes are used for different ions.

The membrane is in contact with an internal electrode conductor element, such as for example Ag—AgCl, connected to the electrode lead, which is connected to the pH or concentration meter. The voltage, which will develop for the ISE electrode, is a function of the ion sensitive membrane. Response of the electrode may be described as the voltage developed between the inside and the outside of the ion sensitive membrane. The ion sensitive membrane composition will determine the electrode's response time and its sensitivity to other ions.

An ISE works on the basic principal of a galvanic cell. By measuring electric potential generated across a membrane by selected ions, and comparing it to a reference electrode, a net charge is determined. The strength of this charge is directed proportional to the concentration of the selected ion.

The sensing part of the electrode is usually made from an ion specific membrane, coupled together with a reference electrode (either separate or in combination). ISE's may incorporate their own reference electrode; these are usually either a single junction refillable type Ag/AgCl type, or a double junction type, which is used for ISE's such as chloride, bromide, and the like. These types of reference electrodes allow the user to select an appropriate electrolyte for the particular application. For instance, potassium nitrate is used as a filling solution for ISE's for Chloride, Bromide, Iodide, Cyanide, Silver, and Sulfide.

In one embodiment, a sodium ISE is fixed at an in-flow of an ion exchanger column to measure an influent fluid stream, and another sodium ISE is fixed at an out-flow to measure an effluent fluid stream. For the regenerated/fresh ion exchange column in the sodium form, the differential sodium calculated from these two measurements can be used to calculate the total hardness in the feed water.

In a second embodiment, a single (sodium) ion exchange electrode and a valve mechanism is utilized. This embodiment provides for: a) feed (hard) water to the sensor for a sodium measurement; b) softened water to the sensor for a sodium measurement; and c) the calculation of the differential between the measured sodium and total hardness.

The present invention may be described as an apparatus employing a methodology for determining total hardness in a fluid stream utilizing an ion exchange column in a monovalent cationic form having an inlet and an outlet, where one or more monovalent ion selective electrodes are positioned either at an inlet, outlet, or at both locations simultaneously. The monovalent cation selective electrode is in fluid communication with one or more valves incorporated within a fluid path in order to introduce feed water or softened water to the monovalent cation selective electrode. Additionally, one blending valve may be incorporated in the ion exchange column to allow a fraction of the feed (hard) water to mix with a fraction of the softened water. In this manner, the blending valve may be utilized to adjust the hardness of the water at the output.

Preferably, the monovalent cation selective electrode (ISE) is one of a cation selected from the group of elements comprising hydrogen, sodium, or potassium. Sodium is presented in the description below as an exemplary embodiment; however, the other aforementioned elements may be used without compromising the differential methodology presented.

An ISE typically presents millivolts (mV) output for a given element (ion) concentration. In one embodiment, the sensor comprises three chambers: (a) a working electrode in contact with a conductive solution and with an ionophore membrane barrier; (b) a reference electrode in contact with KCl and bound by a dialysis membrane; and (c) a chamber between the two membranes where sample fluid can be introduced for measurement and dispensed, and such that there is electrical continuity from the working electrode, through the conductive solution, an ionophore membrane, the sample fluid for analysis, the dialysis membrane, the KCl solution, and to the reference electrode. Feed water is fed into the chamber, where sodium ($Na^+$) is measured, then soft water is introduced into the sensor and sodium is again measured. The ISE produces a voltage that correlates to the concentration of the relevant monovalent ion. The voltage is used to determine the true concentration of the ion.

Referring to FIGS. 1-4, electrodes 1a, 1b of a differential sodium ISE sensor cassette 10 of an embodiment of the present invention described herein have the advantage of providing reproducible potentiometric determinations of ion activity, while eliminating the requirement for wet storage or preconditioning prior to use and thus may function without the use of a reference electrode. In addition to this advantage, the present invention also addresses any need to calibrate the electrodes and, with the internal filling solution trapped within the electrode (completely sealed from the external world, no evaporation or loss of internal filling solution), ensures an extended life of the electrode.

Figure 1:
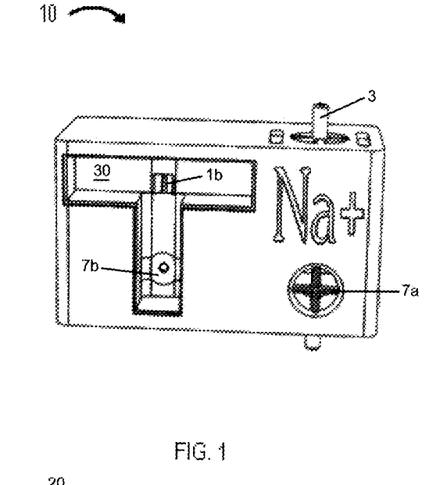
FIG. 1 is a perspective view of an embodiment of an ISE sensor cassette of the present invention.
Figure 2:
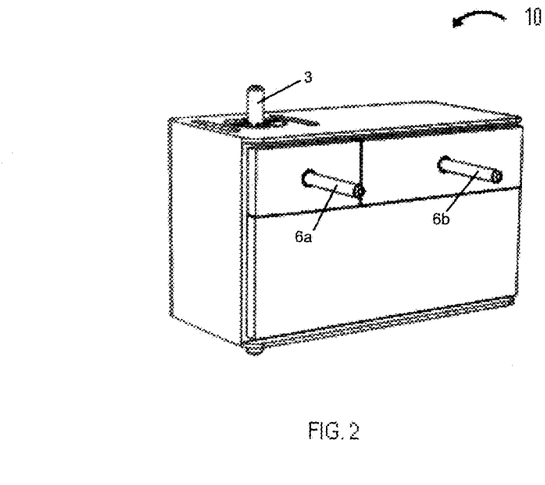
FIG. 2 is a rear perspective view of the ISE sensor cassette of FIG. 1.
Figure 3:
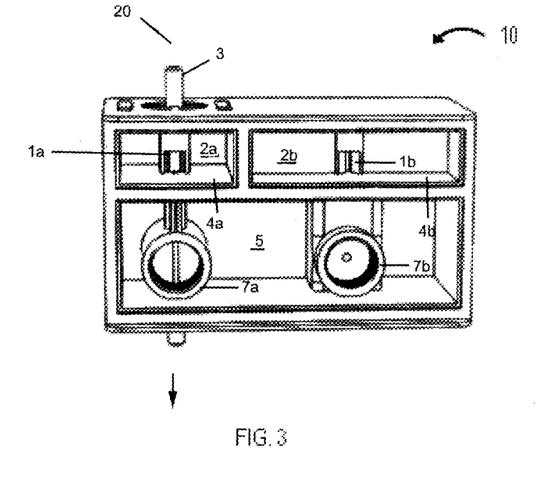
FIG. 3 is a rear cutaway view of the ISE sensor cassette of FIG. 1.
Figure 4:
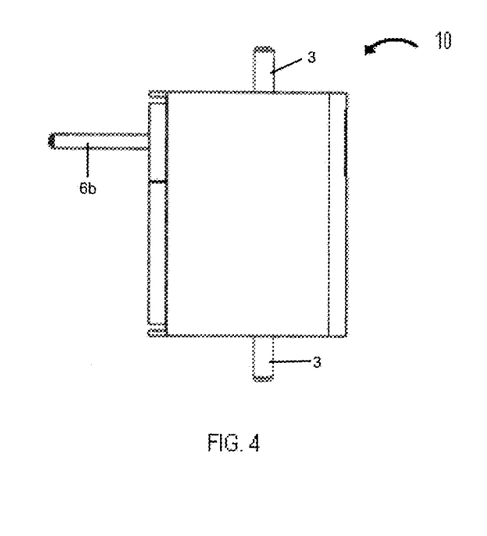
FIG. 4 is a side view of the ISE sensor cassette of FIG. 1.
Figure 5:
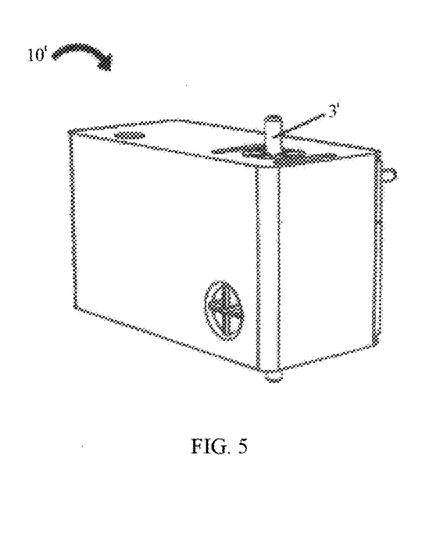
FIG. 5 is a perspective view of another embodiment of an ISE sensor cassette of the present invention.
Figure 6:
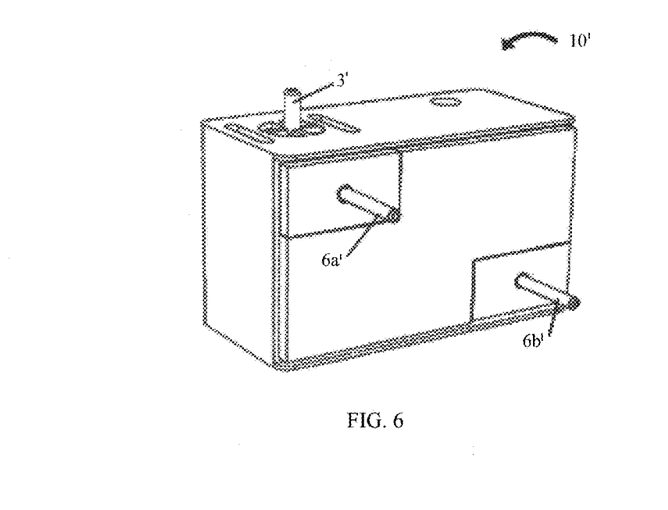
FIG. 6 is a rear perspective view of the ISE sensor cassette of FIG. 5.
Figure 7:
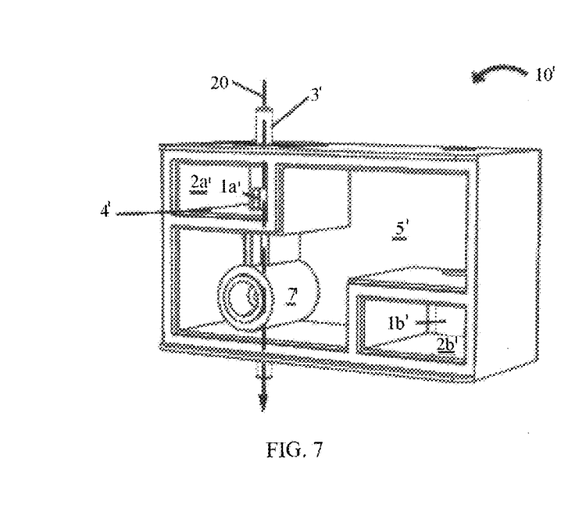
FIG. 7 is a rear perspective cutaway view of the ISE sensor cassette of FIG. 5.
Figure 8:
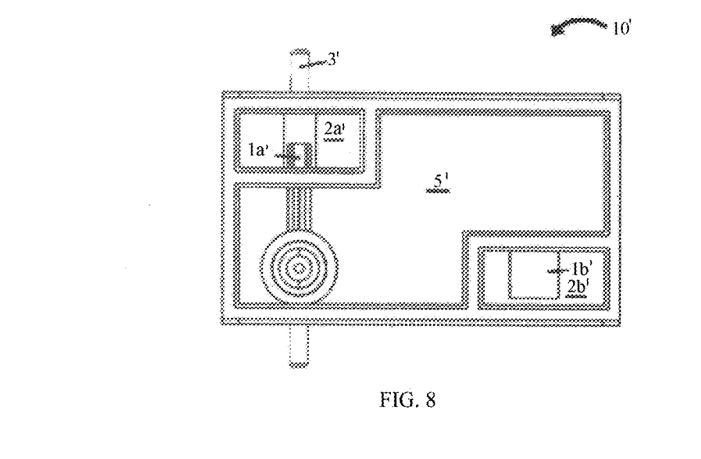
FIG. 8 is another rear cutaway view of the ISE sensor cassette of FIG. 5.
Figure 9:
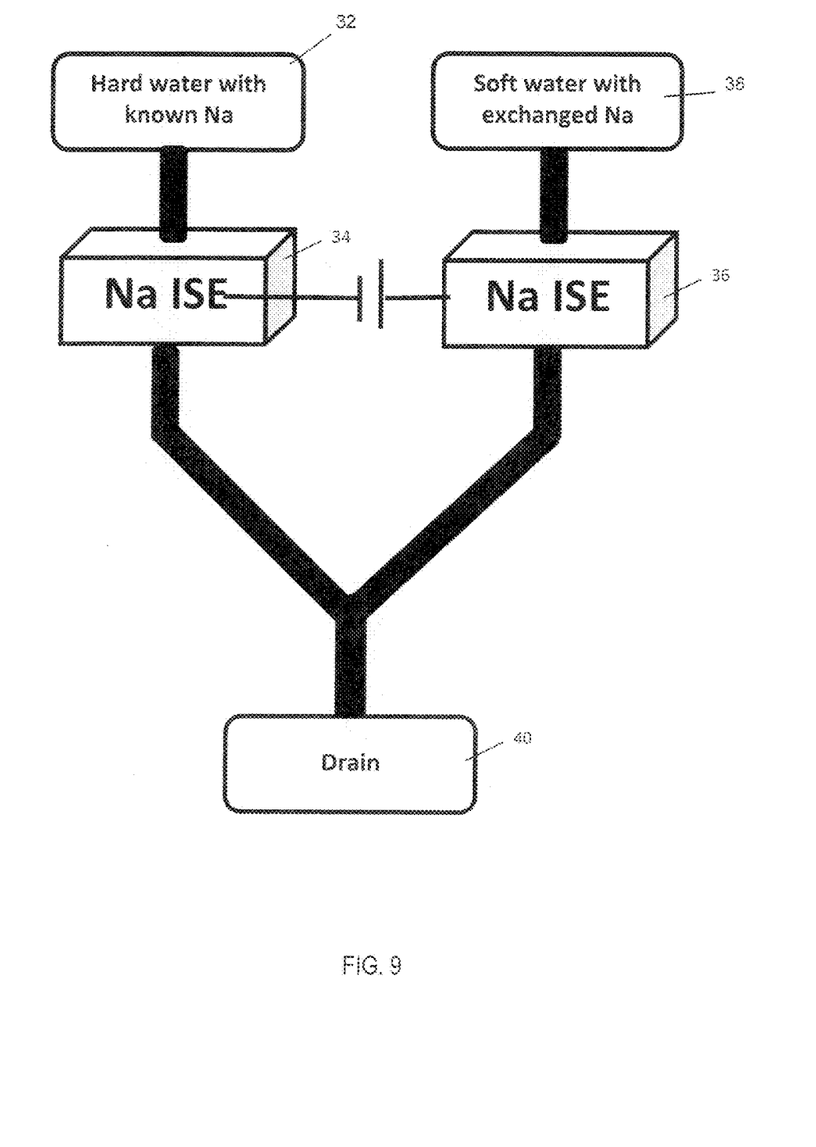
FIG. 9 is a diagram of a second embodiment of the system of the present invention.

FIG. 1 is a perspective view of an embodiment of an ISE sensor cassette 10 of the present invention depicting the front side of the cassette. FIG. 2 is a rear perspective view of the ISE sensor cassette 10 of FIG. 1. FIG. 3 is a rear cutaway view of the ISE sensor cassette 10. FIG. 4 is a side view of the ISE sensor cassette of FIG. 1.

In the embodiment of FIGS. 1-4, the electrodes 1a, 1b (also known as "flow through electrodes") have two identical respective chambers 2a, 2b. A sodium ("Na") selective membrane 3 is shaped in a tubular form to create a 360 degree engagement with a sample fluid stream that flows through it in the direction of arrow 20. The tubes are made in similar fashion and are isolated from a PVC resin used for the electrode body preferably using a neutral 100% pure PVC plasticized membrane. The electrode is completed by inserting two dialysis membranes 4a, 4b (one for each chamber) to create a salt bridge 5 to complete the fluidic connectivity. A dialysis membrane is a semi-permeable film containing various sized pores. Molecules larger than the pores cannot pass through the membrane but small molecules can do so freely.

The electrode chambers 2a, 2b are designed to hold 2-4 mL of internal filling solution. The measurement of voltage potential in millivolts ("mV") is accomplished between two Ag/AgCl pins 6a, 6b of the two $Na^+$ electrodes 1a, 1b. The pretreated hard water is aspirated through the first chamber 2a followed by post-treated soft water. The analysis of the pre-treated hard water—depending on its water source—provides the presence of the sodium (baseline) in the water source. Analysis of the post-treated soft water provides the increase in sodium ions (exchanged during softening process), after correcting for the baseline sodium. Valves 7a, 7b are disposed beneath the $Na^+$ electrodes 1a, 1b, respectively, and at least one of these valves are for introducing feed water or softened water to the ISEs.

The cassette 10 of the present invention does not need any calibration with any standards solutions and is maintenance-free. Extended life thus results since there is no need for a reference electrode, and the entire cassette 10 is purely sealed to avoid any potential loss of internal filling solution or the salt bridge 5 solution. In addition to the present invention having differential electrodes, it also addresses the baseline drift (measured in mV) since both electrodes drift in the similar fashion over the period of time, negating any effect that could arise from the baseline drift.

Figure 14:
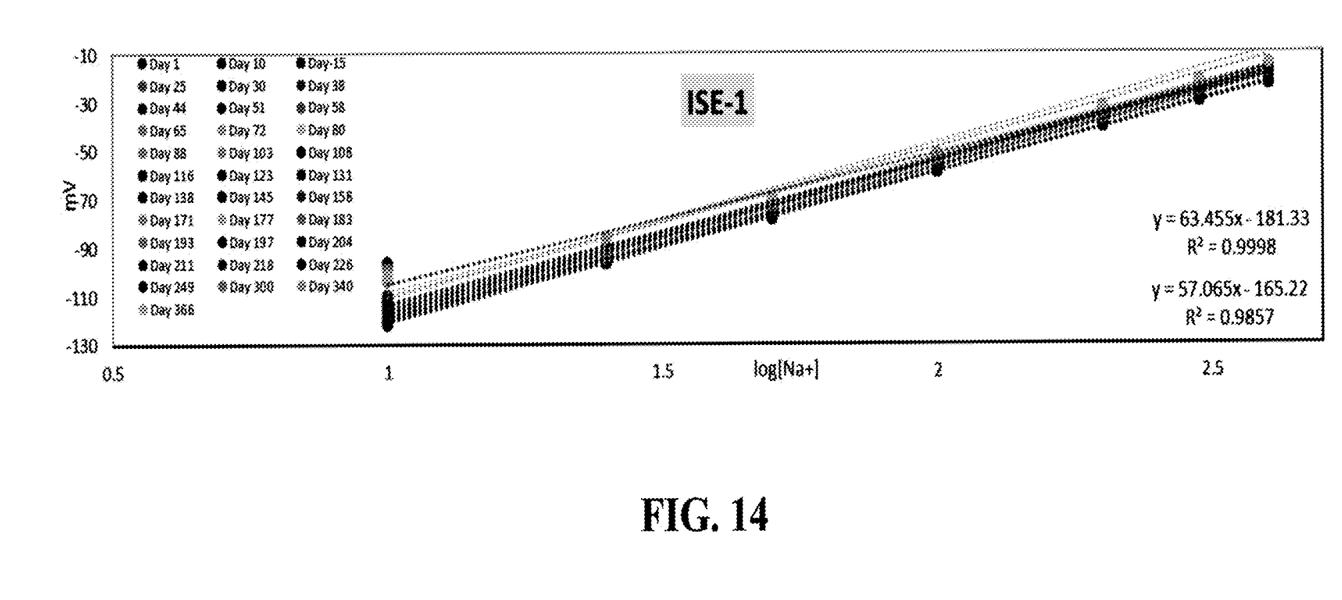
FIG. 14 is a graph of calibration stability and repeatability of a sodium ISE sensor over the course of one year.

FIG. 14 is a graph of a calibration plot of a Sodium ISE sensor of the present design depicting predictive, linear repeatability and reproducibility over a one year period. The sodium ISE sensor calibration was performed by recording corresponding millivolts of Na-ISE for sodium solutions of 10-400 ppm concentrations.

Table II below depicts drift measurements over the same time period. Empirical data for the drift in slope (M) and intercept (b) is presented at 5 different time intervals from day 3 to day 366 for three ISE sensors (ISE 1, ISE 3, and ISE 6).

TABLE II

| | Day 3 | | | Day 300 | | | Day 300- Drifts from Day 3 | | | Day 366 | | | Day 366- Drifts from Day 3 | | |
| --- | --- | --- | --- | --- | --- | --- | --- | --- | --- | --- | --- | --- | --- | --- | --- |
| | M | b | TH | M | b | TH | M | b | TH | M | b | TH | M | b | TH |
| ISE 1 | 63.385 | 182.14 | 25.4 | 61.846 | 172.57 | 26.5 | 1.5 | 9.6 | 1.1 | 57.065 | 165.22 | 28.5 | 6.3 | 16.9 | 3.0 |
| ISE 3 | 62.634 | 178.26 | 24.2 | 67.382 | 187.04 | 23.7 | 4.7 | 8.8 | −0.5 | 57.158 | 164.98 | 26.8 | −5.5 | −13.3 | 2.7 |
| ISE 6 | 61.355 | 176.16 | 25.6 | 66.407 | 187.88 | 21.6 | 5.1 | 11.7 | −4.0 | 57.817 | 172.2 | 23.5 | −3.5 | −4.0 | −2.2 |

The electrodes and devices of this invention can be used to determine the change in concentration of a selected ion, such as sodium ions, in any aqueous liquid that undergoes a change (increase or decrease) in ionic concentration when the influent fluid is treated or processed. Relevant applications may include, but are not limited to: reverse osmosis ("RO") water, waste water, cooling water, ground water, milk (dairy farm), di alysis/dialysate, desalination plant, food, and brewery processing fluids, to name a few.

The two sodium electrodes 1a, 1b are made in similar fashion and mimic each other in terms of baseline drift and slope drift. In the embodiment of FIGS. 1-4, the two electrodes 1a, 1b are housed in the cassette 10 in chambers 2a, 2b respectively, with an in-built salt bridge 5. The salt bridge is created by the interfacing dialysis membranes 4a, 4b between the two respective flow paths. One electrode 1b is in constant contact with an in-built, contained sodium standard solution 30 (e.g., at a concentration of 500 ppm), acting as a pseudo reference electrode. Having two similar sodium electrodes in tandem addresses the mV drift typically observed in conventional ISE technology and this differential sodium electrode enables the present invention to make measurement with factory preset slope and intercept programmed into the cassette. Since the electrodes are constantly exposed to water (lacking any lipophilic constituents), the leaching of the ionophore is not expected, which has been the typical mode of failure of the electrodes, as well as the slope drift, found in the prior art.

In a second embodiment represented by FIGS. 5-8, the cassette 10' has two Ag/AgCl pins 6a', 6b" located on an upper left and lower right corners of the cassette 10', respectively, and are diagonal from each other. Sodium electrode 1a' measures the sodium concentration of the sample solution (hard and soft water), and sodium electrode 1b' is immersed in a calibrating standard in compartment 2b' which has a known amount of sodium. The difference in the differential measurement (in mV) provides the exact amount of sodium in hard/soft water in comparison with the sodium present in the calibrating standard reservoir.

The different compartments 2a', 2b' built into the cassette 10' receive the electrodes 1a', 1b' respectively, A sodium membrane 3' runs vertically through the cassette 10' on one side of the cassette (here depicted on the left side), entering through the compartment 2a" and extending out the bottom of the cassette. A valve 7' is disposed within the path of the sodium membrane 3' directly beneath compartment 2a' and introduces feed water or softened water to the ISE.

The composition of a salt bridge 5' disposed in the middle of the cassette is 2M KCl which helps to minimize the liquid junction potential, keeping in mind there are as many as two junctions with varying ionic compositions separated by the dialysis membrane. The amount of 2 M KCl in the salt bridge 5 may be approximately 10-12 mL.

A sodium standard solution of 500 ppm needs to be made in 2 Molar KCl, to avoid any drift that could arise from the diffusion of KCl from the salt bridge 5' via the dialysis membrane 4', and the 2 Molar KCl solution needs to have 500 ppm of NaCl to avoid the diffusion of NaCl from the standard solution into the salt bridge 5'. Diffusion of NaCl would in turn reduce the concentration of the $Na^+$ in the standard solution and create the electrode drill.

Several embodiments of the above described present invention may be employed. In the embodiment presented in FIG. 9, hard water with known sodium 32 flows through a sodium ISE sensor 34 on one side, which is in electrical communication with a second sodium ISE sensor 36 through which soft water having an exchanged sodium 38 flows through. The out-flow from both of these sodium ion-selective electrodes meet at a shared drain 40, which provides the electrical connectivity for measuring the mV difference between the sodium ISE exposed to hard water with known Na and the sodium ISE exposed to soft water with exchanged Na ($Na^+_{exchanged}$). The mV difference could be used to calculate the amount of sodium ions exchanged which would in turn provide the information about the hardness of water (total calcium and magnesium concentration). This configuration may be employed within the ISE cassette of FIG. 1.

Figure 10:
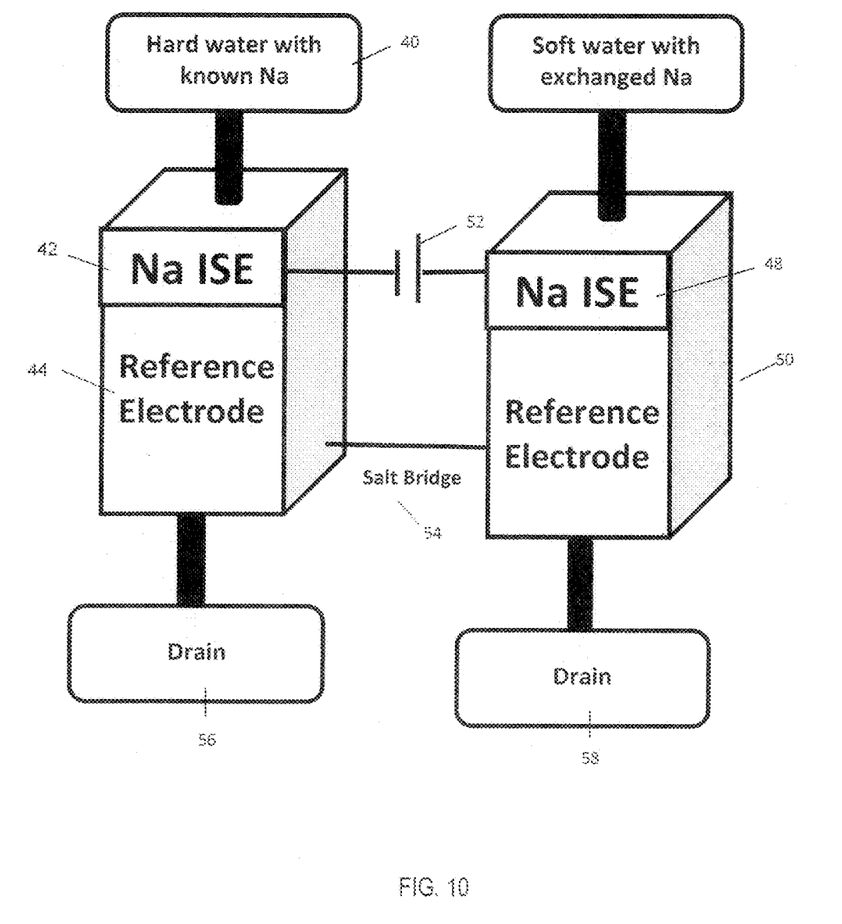
FIG. 10 is a diagram of a third embodiment of the system of the present invention.

In the embodiment presented in FIG. 10, hard water with known sodium 40 flows through a sodium ISE sensor 42 coupled with a reference electrode 44. Soft water with exchanged sodium 46 flows through a second sodium ISE sensor 48 coupled with a second reference electrode 50. Both sodium ISEs sensors 42, 48 are in electrical communication 52, and their respective reference electrodes 44, 50 employ a salt bridge 54 between them. These combined sodium ISE sensors 42, 48 and reference electrodes 44, 50 output to separate drains 56, 58 respectively (or share a drain). In this design each sodium ISE is a standalone system and can provide the Na value in the solution that is passed through it and at the same time, by connecting with a salt bridge could function as a differential sodium ISE.

Figure 11:
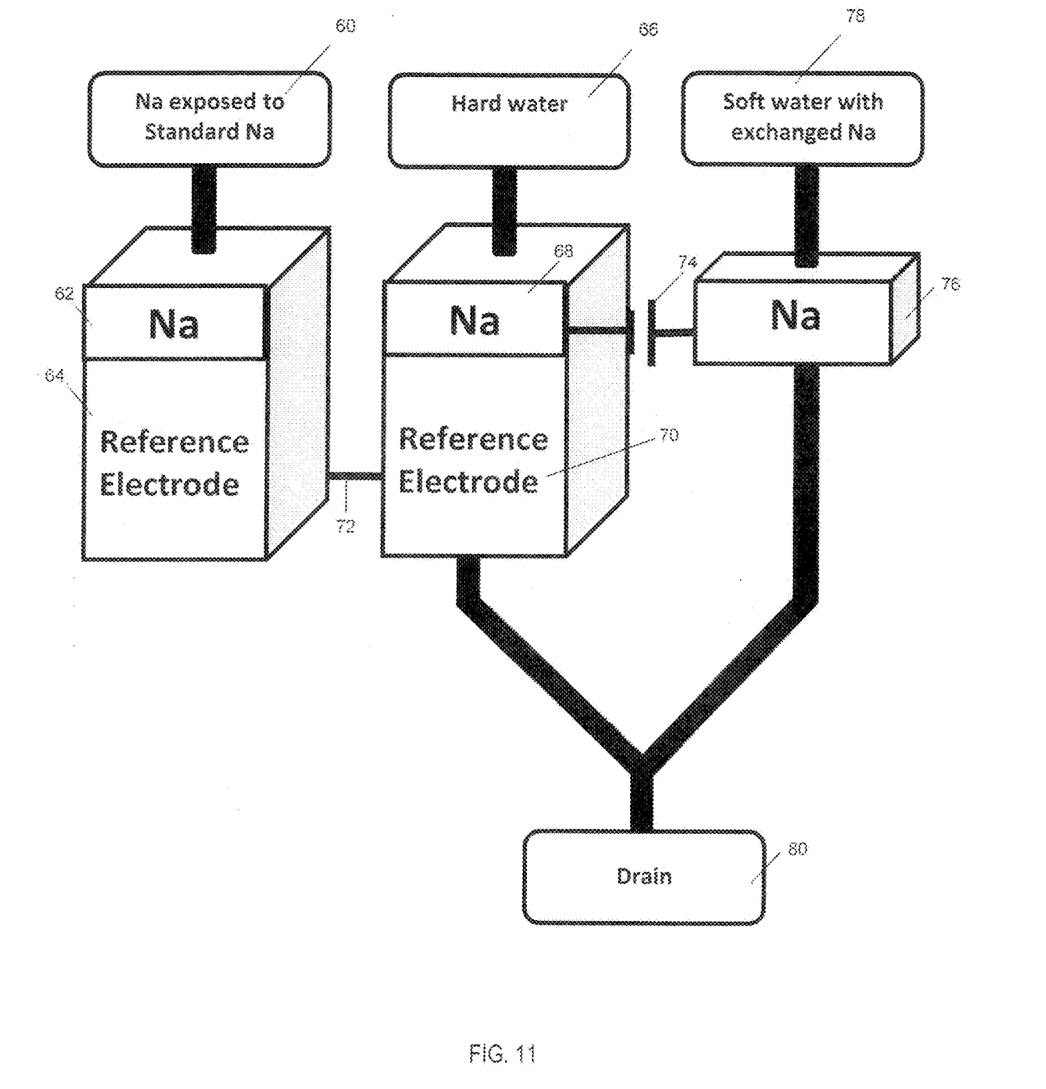
FIG. 11 is a diagram of a fourth embodiment of the system of the present invention.

In the embodiment presented in FIG. 11, sodium exposed to standard sodium 60 flows through sodium ISE sensor 62 coupled with a reference electrode 64. Hard water 66 flows through a second sodium ISE sensor 68 coupled with its own reference electrode 70, where reference electrode 70 employs a salt bridge 72 between itself and the reference electrode 64. The second sodium ISE sensor 68 is in electrical communication 74 with a third sodium ISE sensor 76. Soft water with exchanged sodium 78 flows through this third sodium ISE sensor 76. The pair of the second sodium ISE sensor 68 and corresponding reference electrode 70 (receiving the hard water), and electrically connected sodium ISE sensor 76 (receiving the soft water with exchange Na), both may out-flow at a shared drain 80. In this set up the first sodium electrode which is exposed to standard sodium serves as calibrated Na electrode as it is exposed to solution with known sodium and serves as a reference point to compare the sodium in hard water whose sodium concentration might not be known.

Figure 12:
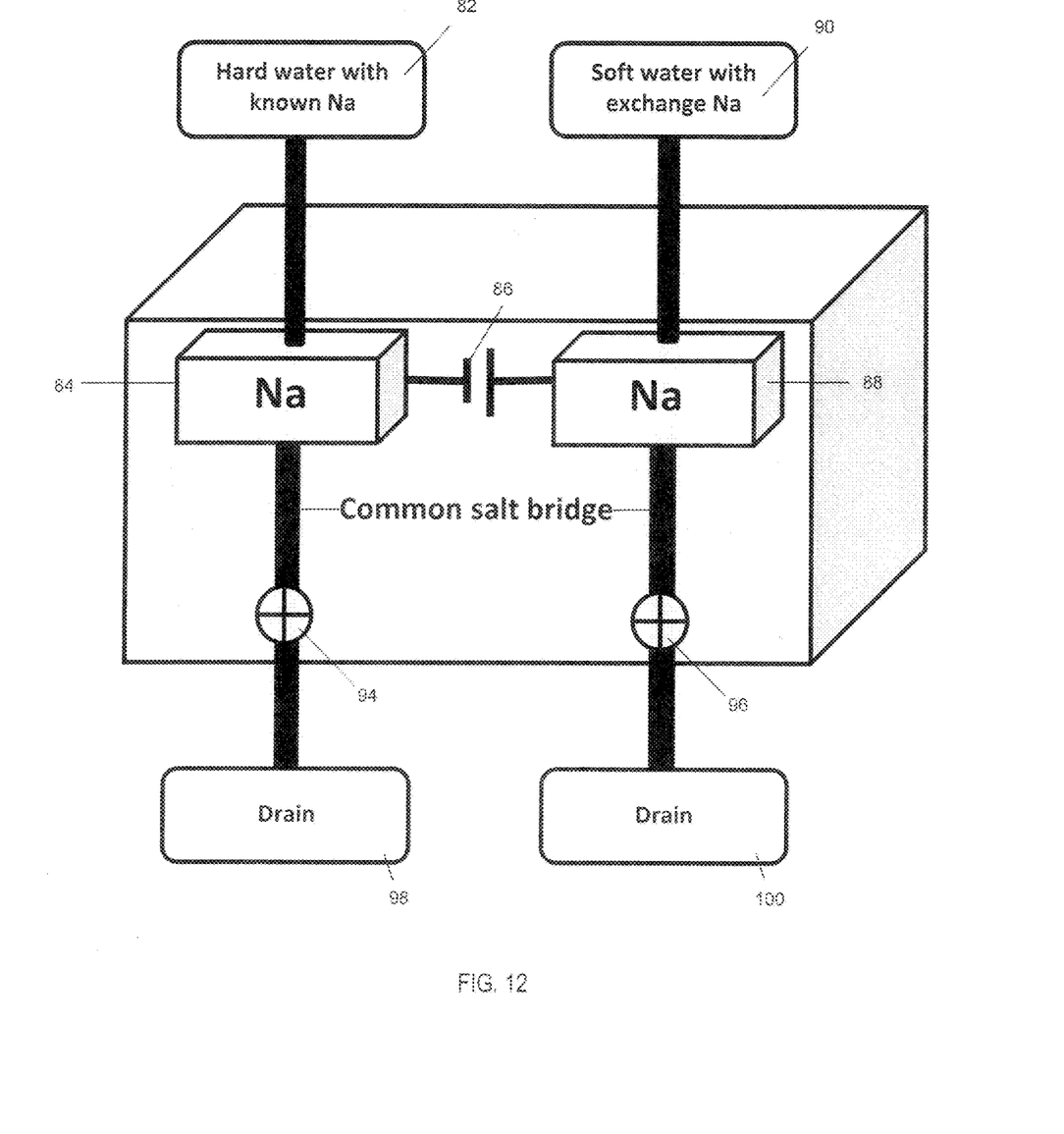
FIG. 12 is a diagram of a fifth embodiment of the system of the present invention.

In the embodiment presented in FIG. 12, hard water with known sodium 82 flows through a sodium ISE sensor 84 in electrical communication 86 with another sodium ISE sensor 88 through which soft water with exchange sodium 90 flows. Both sodium ISE sensors 84, 86 share a common salt bridge 92. All such elements of this embodiment are preferably encased in a cassette, such as the cassette case of FIG. 1. Valves 94, 96 are disposed at the out-flow paths of both sodium ISE sensors 84, 86, adjacent to respective drains 98, 100 for each ISE sensor.

Figure 13:
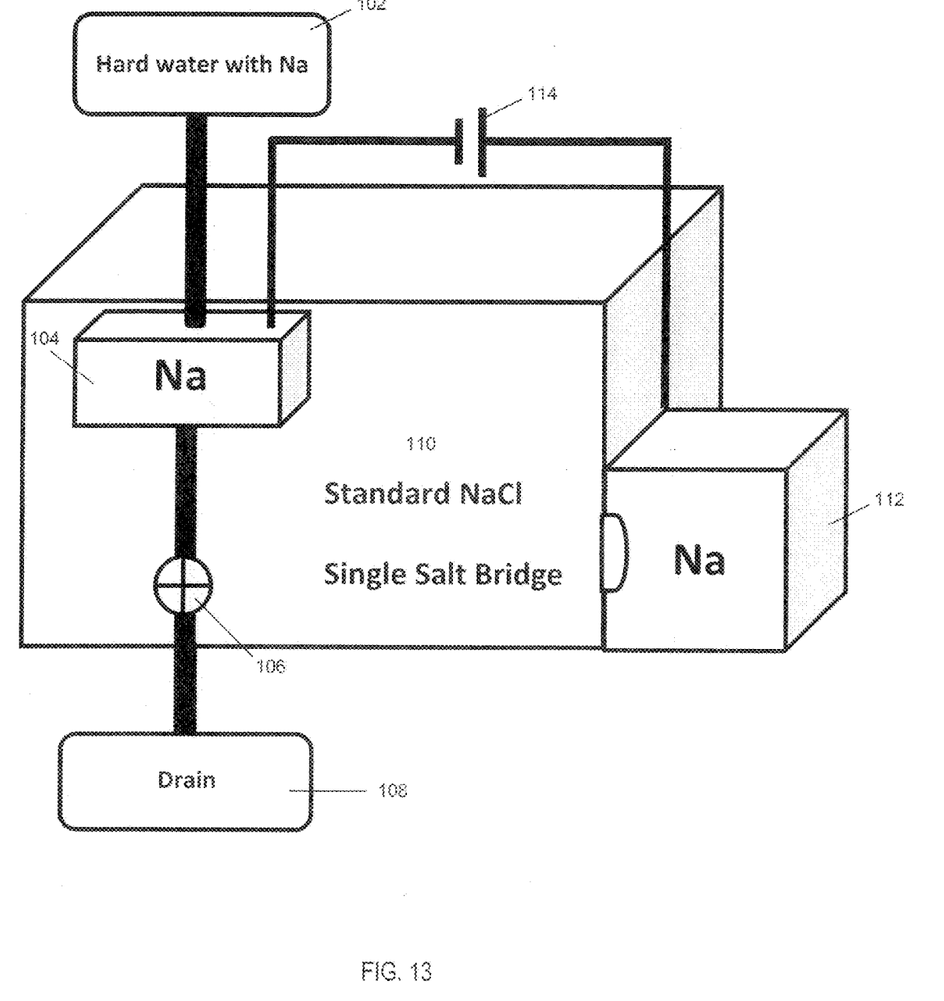
FIG. 13 is a diagram of a sixth embodiment of the system of the present invention.

In the embodiment presented in FIG. 13, hard water with sodium 102 flows through a sodium ISE sensor 104. A valve 106 is disposed at the out-flow path of the sodium ISE sensor 104, adjacent to its respective drain 108. The sodium ISE sensor 104 is encased in a cassette (not shown) containing a standard sodium chloride single-salt bridge 110. A separate sodium ISE sensor 112 is disposed outside of the cassette and is in electrical communication 114 with the first sodium ISE sensor 104.

In yet another embodiment, hard water and soft water upstream and downstream, respectively, of ion exchange column is allowed to pass through a single ISE or ISE coupled with reference electrode and then to drain.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A cassette for measuring the total hardness in a fluid stream, comprising:
   a housing;
   an ion exchange column or vessel in a monovalent cationic form, the ion exchange column or vessel having an inlet and an outlet separately disposed and extending through the housing; and
   first and second monovalent cation selective electrodes positioned within the housing and extending therefrom, said first and second monovalent cation selective electrodes capable of measuring monovalent cation activity, quantity, or concentration in a fluid stream;
   said housing configured into a plurality of chambers, said first and second monovalent cation selective electrodes each housed within one of said plurality of chambers, wherein one of said chambers housing said first monovalent cation selective electrode is filled with an internal solution;
   a selective membrane shaped to create engagement with a fluid sample flowing therethrough;
   a dialysis membrane in each of said plurality of chambers forming a salt bridge between said first and second monovalent cation selective electrodes; and
   an Ag/AgCl pin for each of said first and second monovalent cation selective electrodes.

2. The cassette of claim 1 wherein said salt bridge is formed by the interfacing of said dialysis membranes between two respective flow paths.

3. The cassette of claim 1 wherein said first and second monovalent cation selective electrodes are configured to measure sodium ions (Na+).

4. The cassette of claim 3 wherein said internal solution comprises a sodium standard solution having a known amount of sodium.

5. The cassette of claim 4 wherein said sodium standard solution comprises 500 ppm sodium formed in 2 M KCl.

6. The cassette of claim 1 wherein said internal solution is in constant contact with said first monovalent cation selective electrode.

7. The cassette of claim 1 wherein said selective membrane is a sodium membrane.

8. The cassette of claim 7 wherein said selective membrane traverses said cassette vertically, entering through at least one of said plurality of chambers, and extending to the edge of said cassette or outside said cassette.

9. The cassette of claim 1 including a valve disposed within a fluid path of said selective membrane, said valve configured to introduce fluid to at least one monovalent cation selective electrode.

10. The cassette of claim 9 wherein said valve is configured to introduce feed water or softened water to the at least one monovalent cation selective electrode.

11. The cassette of claim 1 wherein the ion exchange column further comprises at least one blending valve to allow a fraction of a hard water fluid stream to mix with a fraction of a softened water fluid stream.

12. The cassette of claim 11 wherein the at least one blending valve further adjusts hardness of hard water at the outlet.

13. The cassette of claim 1 wherein said first and second monovalent cation selective electrodes comprise hydrogen, sodium, or potassium.

14. The cassette of claim 1 wherein said salt bridge comprises 2 M KCl to minimize liquid junction potential.

15. The cassette of claim 1 wherein at least one of said first and second monovalent selective electrodes is coupled to a reference electrode.

16. The cassette of claim 1 wherein at least one of said first and second monovalent selective electrodes is shaped in tubular form to create a 360 degree engagement with a fluid sample flowing therethrough.

17. The cassette of claim 1 wherein said first and second monovalent selective electrodes are coupled to first and second reference electrodes, respectively.

18. The cassette of claim 1 including:
a third monovalent cation selective electrode configured to receive soft water with exchanged sodium; and
at least one drain to receive outflow from effluent fluid from said second and third monovalent cation selective electrodes.

19. The cassette of claim 1 wherein at least one of said monovalent cation selective electrodes is positioned within the housing at said inlet or said outlet.

20. The cassette of claim 1 wherein hard water flows through a water softener via the inlet and outlet to be measured by at least one of said monovalent cation selective electrodes, which provides an electrical signal commensurate with the amount cation concentration measured at said inlet and at said outlet to provide for a differential measurement of these values in order to ascertain the amount of cation being generated by said softener.

21. The cassette of claim 1 wherein said monovalent cation selective electrodes are capable of measuring ionic species that will affect capacity of said softener, including iron that permanently exchanges in a cation resin bed in said softener.

22. The cassette of claim 1 wherein the amount of cation concentration measured at said outlet is a measure of an amount of cation in said water, such that said apparatus includes a bypass control to allow unsoftened water to be blended to reduce the amount of said cation in the water, or to regulate the amount of hardness in the output.

* * * * *

UNITED STATES PATENT AND TRADEMARK OFFICE
CERTIFICATE OF CORRECTION

| | | |
|---|---|---|
| PATENT NO. | : 11,016,074 B2 | Page 1 of 1 |
| APPLICATION NO. | : 16/369925 | |
| DATED | : May 25, 2021 | |
| INVENTOR(S) | : Malcolm Kahn et al. | |

It is certified that error appears in the above-identified patent and that said Letters Patent is hereby corrected as shown below:

In the Specification

Column 10, Line 32, delete "di alysis/dialysate" and substitute therefor -- "dialysis/dialysate" --

Column 11, Line 2, delete "2a"" and substitute therefor -- "2a'" --

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*